US006658088B2

(12) United States Patent
Tiren

(10) Patent No.: US 6,658,088 B2
(45) Date of Patent: Dec. 2, 2003

(54) MINIATURE X-RAY SOURCE AND METHOD

(75) Inventor: Jonas Tiren, Uppsala (SE)

(73) Assignee: Radi Medical Technologies AB, Uppsala (SE)

( * ) Notice: Subject to any disclaimer, the term of this patent is extended or adjusted under 35 U.S.C. 154(b) by 314 days.

(21) Appl. No.: 09/792,072

(22) Filed: Feb. 26, 2001

(65) Prior Publication Data

US 2002/0054664 A1 May 9, 2002

Related U.S. Application Data

(60) Provisional application No. 60/246,723, filed on Nov. 9, 2000.

(51) Int. Cl.[7] ........................ H01J 35/00
(52) U.S. Cl. ........................ 378/119
(58) Field of Search ........................ 378/119, 120, 378/121, 122, 123, 137, 143

(56) References Cited

U.S. PATENT DOCUMENTS 4,426,722 A * 1/1984 Fujimura .................... 378/137
4,958,365 A * 9/1990 Sohval et al. ............... 378/122
5,854,822 A 12/1998 Chornenky et al. ......... 378/122
5,940,469 A * 8/1999 Hell et al. .................. 378/143
5,984,853 A 11/1999 Smith ............................ 600/1
6,064,718 A * 5/2000 Holland et al. ............. 378/122
6,148,061 A * 11/2000 Shefer et al. ............... 378/121
6,159,140 A * 12/2000 Loeffler et al. ................ 600/3
6,188,746 B1 * 2/2001 Miley et al. ................ 378/119
6,353,658 B1 * 3/2002 Trebes et al. ............... 378/123

* cited by examiner

*Primary Examiner*—Max Noori
(74) *Attorney, Agent, or Firm*—Foley & Lardner

(57) ABSTRACT

A miniature X-ray source includes a support structure provided with a through hole, an anode arranged at one end of the hole and a cathode at the other end of the hole, thereby defining a cavity, wherein the anode and cathode are adapted to be energized to generate X-ray radiation. The support structure has a cross-sectional shape that is determined such that a desired radiation distribution of the radiation generated by the X-ray source is achieved. Also a method of manufacturing miniature X-ray sources is disclosed.

26 Claims, 3 Drawing Sheets

8 2 6 4 20kV 10

X1 X2

12 14 16

MINIATURE X-RAY SOURCE AND METHOD

The applicant hereby claims the benefit of U.S. Provisional Application No. 60/246,723, filed Nov. 9, 2000. The entire content of this provisional application is incorporated herein by reference.

FIELD OF THE INVENTION

The present invention relates to a miniature X-ray source and to a method of manufacturing miniature X-ray sources.

BACKGROUND OF THE INVENTION

In treating stenosis in coronary arteries, a restenosis occurs in 30–60% of the cases. It is known that a treatment with beta- or gamma-(X-ray) radiation will decrease the occurrence of restenosis substantially.

Another example of an application of the present invention is treatment of cancer tumors where it is desired to deliver radiation locally.

Methods to apply the radiation to the site of treatment are presently subject to intensive research. Generally, a hollow catheter is inserted into the body, typically via an artery, in such a way that its distal end is placed near the site of treatment. A source of radiation attached to the distal end of an elongated member is inserted into the hollow catheter, and. is forwarded until the radiation source is disposed at a proper position for radiating the site of treatment. In the specific case of treating cardiac vessels, the catheter is placed near the cardiac vessel tree (this catheter is often called a "guide catheter"). A very thin wire—called a guide wire—is then used to probe further and reach the site where treatment shall be performed. The therapeutic device is moved along this wire, i.e. by threading the device onto the guide wire. It is obvious that the therapeutic device has to have a hole close to its distal end in order to do this.

Radiation treatment methods using radioactive pellets or balloons etc. as a radiation source is known in the art. Since these methods have some drawbacks, such as the need for substantial efforts to control radiation in the environment outside the patient, the use of a miniature electrical X-ray source including a cold cathode has been proposed. Such a source may be switched on and off due to its electrical activation. An example of such an X-ray source is described in the U.S. pat. No. 5,854,822 as well as in U.S. Pat. No. 5,984,853.

U.S. Pat. No. 5,984,853 discloses a method and apparatus of creating a miniturized source of radiation and delivering radiation to a location such as a therapy location. The radiation source is built up from two plates with a recessed region forming a microcavity at one or several localities. An anode material and a cathode with extremely small dimensions, and having the form of a sharp tip, are located within this microcavity. During the manufacturing process lithographic and etching techniques according to well-known techniques are used to define the structures of the microcavity, the anode and the cathode. By using the above-mentioned fabrication techniques the manufacturing cost per unit becomes very small when the elements are fabricated in large numbers. This is due to the fact that batch fabrication with thousands of units per batch is feasible.

However, the apparatus disclosed in U.S. Pat. No. 5,984,853 does not take into account the spatial distribution of the generated radiation.

One object of the present invention is to achieve a structure of an X-ray source allowing manufacturing of a large number of X-ray sources that fulfills requirements regarding radiation distribution of the generated X-ray radiation.

SUMMARY OF THE INVENTION

Conventionally in the semiconductor technology the individual chips obtain a square shape, since it is the most efficient way of cutting (sawing) the wafer, and in addition the wafer is optimally utilized in this way, since no waste is produced.

In order to be able to produce a large number of miniature X-ray sources for the above mentioned type of applications the production is conveniently made in batch processes, starting with a disc-shaped wafer having a diameter of e.g. 4" of a suitable material. Obviously the wafer may also be square or rectangular or polygonal in its shape. By using various techniques known per se from the semiconductor technology, such as lithography combined with etching and deposition techniques, a large number of discrete components can be made from one wafer. Finally, each individual component is cut out from the wafer by e.g. a sawing operation or by laser etching. Other known methods include sawing, blasting and using scribe lines to crack the wafer to discrete parts.

In X-ray radiation therapy inside a living body, and in particular in blood vessels that have a tubular shape, i.e. a circular symmetry, it is desirable that the delivered radiation is uniformly distributed over the irradiated area. In other words it may in this case be desirable that the intensity is essentially equal in all directions.

In addition, sharp edges or corners on miniature X-ray sources should be avoided because these might accidentally damage the vessel or tissue.

By using the manufacturing method according to the present invention a further object may also be achieved, namely a possibility to customize the X-ray source with regard to radiation distribution.

Thus, the manufacturing method according to the present invention is advantageous in at least two aspects: it is a cost-efficient manufacturing method of a large number of X-ray sources and it makes it possible to customize the X-ray source with regard to radiation distribution.

The above-mentioned objects are achieved by a miniature X-ray source and a method of manufacturing miniature X-ray sources according to the present invention.

The present invention provides for a miniature X-ray source including: a support structure provided with a through hole; an anode arranged at one end of the hole and a cathode at the other end of the hole, thereby defining a cavity, wherein the anode and cathode are adapted to be energised to generate X-ray radiation, and wherein the support structure has a cross-sectional shape that is determined such that a desired radiation distribution of the radiation generated by the X-ray source is achieved.

The present invention further provides for a method of manufacturing miniature X-ray sources including the following steps:

i) making through holes, one for each X-ray source to be manufactured, in a disc-shaped support structure wafer having a constant thickness, ii) arranging for each hole an anode and a cathode at opposite sides of the wafer and thereby defining an X-ray source cavity between the anode and the cathode, iii) dividing the wafer into separate elements wherein each element includes an X-ray source and wherein the support structure of each X-ray source has a predefined outer shape that is determined such that a desired radiation distribution of the radiation generated by the X-ray source is achieved.

DETAILED DESCRIPTION OF THE PREFERRED EMBODIMENTS

Figure 1A:
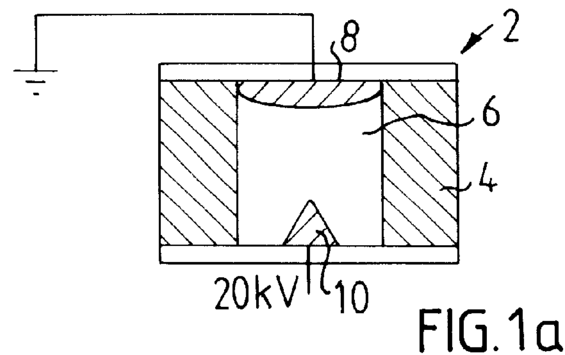
FIGS. 1*a*–1*c* illustrate schematically the structure of a miniature X-ray source manufactured by using the method according to the present invention.

FIG. 1*a* schematically illustrates a miniature X-ray source in across-section, generally designated with reference numeral 2. It comprises a support structure 4 in which an X-ray cavity 6, provided with vacuum, is defined by an anode 10 and a cathode 8 at opposite sides of the cavity. The anode 10 is connected to the positive pole of a high voltage source (not shown), and the cathode 8 is connected to the negative pole or ground.

Figure 1B:
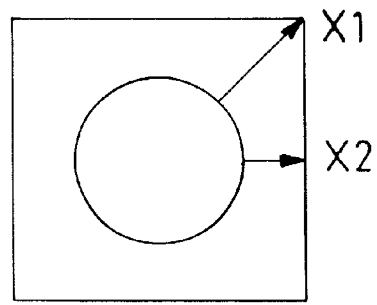
Figure 1C:
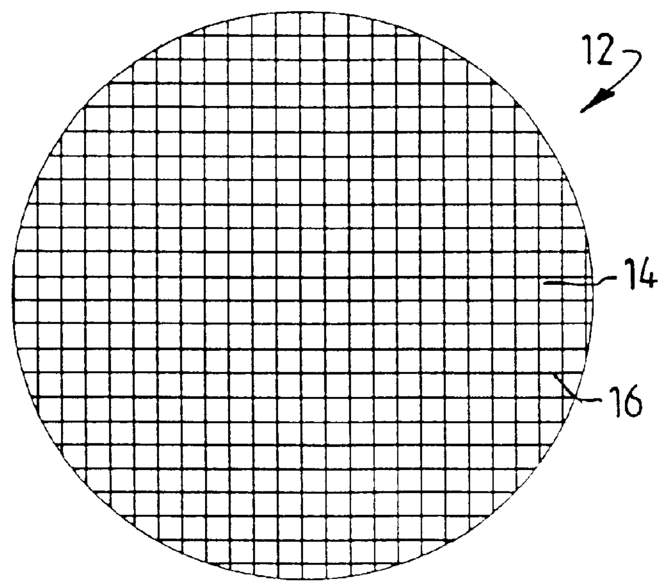

In FIG. 1*b* the device of FIG. 1*a* is shown schematically from above. As can be seen it has a square outer shape. This comes from the standard manufacturing techniques used in semiconductor technology. For example, starting from a circular wafer 12 of a suitable material (see FIG. 1*c*) and processing the wafer 12 according to a number of process steps such as lithographic methods, etching, deposition etc, to create a large number of discrete elements, schematically indicated by reference numeral 14. When the manufacturing process for the discrete elements 14 is completed, sawing along the lines 16 indicated in FIG. 1*c* cuts out each element 14.

For miniature X-ray sources the radiation strength depends upon the level of attenuation in the support structure. The attenuation depends, among other things, on the material of the structure and the distance from the center of the X-ray source the radiation has to travel through the support structure. FIG. 1*b* schematically illustrates different distances X1 and X2 in a square-shaped support structure, resulting in a lower radiation dose being delivered in the direction of X1 than in the direction of X2 due to the higher radiation attenuation in direction X1.

Many different materials may be used, e.g. alumina (polycrystalline $Al_2O_3$), sapphire (crystalline $Al_2O_3$), pyrolytic or cubic boron nitride (BN) or quartz ($SiO_2$).

When determining what material to be used the electrical break-through voltage is of great concern. Namely, the thickness of the material must be dimensioned taking into account the thinnest part of the structure.

Pyrolytic boron nitride is advantageous because it has an acceptable electrical break-through voltage.

It is especially advantageous to choose a material having an intrinsic crystal structure that is the same as the cross-sectional outer shape of the support structure. Both pyrolytic boron nitride and sapphire have a hexagonal crystal structure and by dividing the wafer in hexagonal-shaped structures in the directions that correspond to the crystal structure the intrinsic material characteristics are optimally used.

According to a first aspect of the invention a uniformly distributed radiation around the X-ray source is desired, i.e. having essentially the same level of radiation in each direction in a plane perpendicular to the direction of a through hole in the support structure.

According to a preferred embodiment of the invention the cross-sectional shape of the cavity is circular and the cross-sectional outer shape of the support structure is also circular. These circles are concentric.

However, in order to be able to manufacture large numbers of X-ray sources, the inventor has found that manufacturing techniques used in the semiconductor industry are also applicable for manufacturing X-ray sources.

Although possible to divide a wafer into circular elements it is considered more cost-efficient to divide the wafer along straight lines, preferably by using sawing techniques.

Figure 2A:
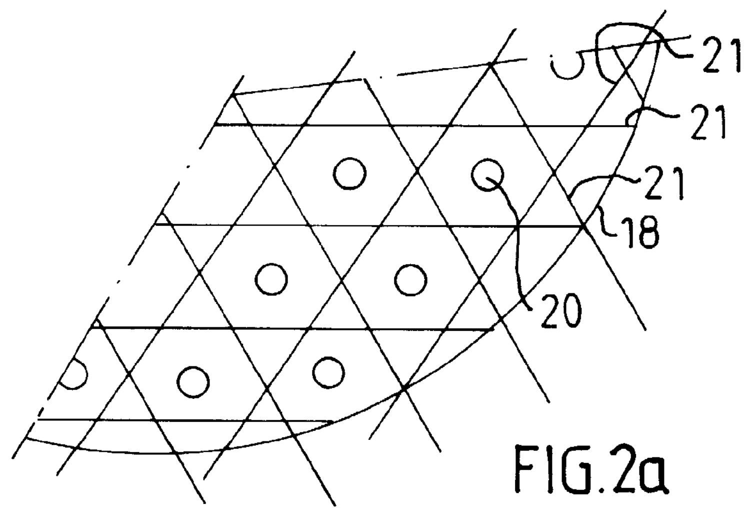
FIGS. 2*a*–2*b* illustrate schematically a part of the manufacture of an X-ray source having a hexagonal outer shape.
Figure 3:
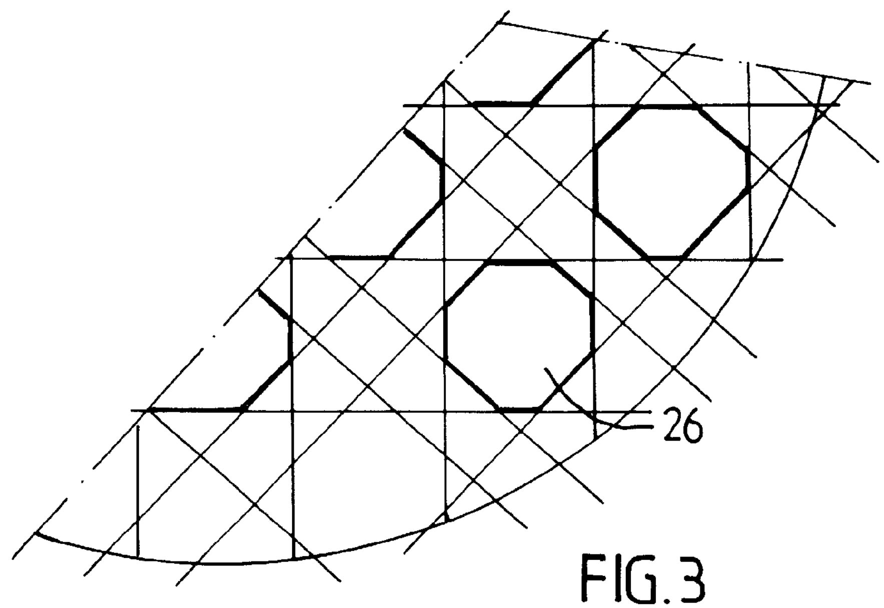
FIG. 3 illustrates schematically a part of the manufacture of an X-ray source having an octagonal outer shape.

FIGS. 2*a* and 3 show two different alternative shapes of the cross-sectional outer shape of the support structure that may be obtained by straight-line divisions of a wafer.

Holes 20 made in the wafer to provide the X-ray source cavities may be achieved in two principally different ways.

Figure 2B:
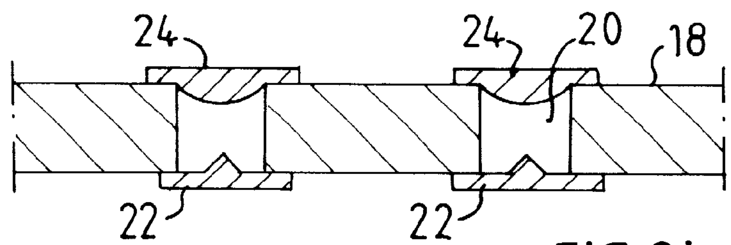

According to a first preferred embodiment in which the cross-section of the cavity is to have a circular shape, the most convenient method is to provide a wafer of a suitable material, e.g. alumina, and to make holes 20 by laser drilling. FIG. 2*a* shows a part of a wafer 18 having holes 20 made by laser drilling. FIG. 2*b* is a cross-section of the wafer 18 in FIG. 2*a*. When the holes 20 are made, cathodes 22 and anodes 24 (FIG. 2*b*) can be mounted in the holes by a suitable bonding method or soldering. Then the wafer 18 is divided as shown in FIG. 2*a* along lines 21 in order to provide X-ray sources having hexagonal cross-sections.

According to a second preferred embodiment in which the cross-section of the cavity is to have a polygonal shape, e.g. hexagonal or octagonal, the holes are made already when the wafer is manufactured. Namely, a positive mold is provided, having protrusions of the desired geometry (polygonal, e.g. octagonal or hexagonal). A ceramic paste is spread on the mold and exposed to sintering conditions. When the mold is removed the wafer will be provided with holes of the desired geometry. In the case of alumina, the wafer may be precision machined (e.g. by drilling, milling etc.) before sintering.

Then, again, cathodes and anodes, shaped as to fit in the holes, are mounted in the holes so as to seal the cavity, and the wafer is divided to produce the polygonal shaped support structures. The anode and cathode structures may also be made as structures on entire wafers, if properly designed with respect to, for instance, thermally induced stress.

If an octagonal cross-sectional outer shape 26 of the X-ray source is desired, the dividing pattern will be as shown in FIG. 3. Obviously this dividing pattern will yield much more waste material, but it may be justified by the shape obtainable being somewhat better suited for the purpose of uniform radiation distribution than the hexagonal dividing pattern shown in FIG. 2*a*.

When the elements have been made as described above, such that they comprise a support structure of e.g. alumina, and an anode and a cathode are mounted in the hole to form the cavity, the X-ray source is completed as follows.

The cavity must be evacuated, which can be achieved with methods known in the art such as by employing evacuation channels and getter materials, and will not be further discussed herein.

According to a preferred embodiment of the invention the individual elements 14 are embedded in a polymer by an injection molding technique, so as to form a "bucket" of plastic around the element 14. Conveniently the mold has a cylindrical shape so as to produce an X-ray source having a generally tubular shape, which is most suitable for insertion into blood vessels which have a generally tubular geometry. However, any shape can be made if desired.

The invention will now be further exemplified by comparisons performed with a square configuration and a hexagonal configuration, respectively.

The following has been used for the examples below: The target tissue is assumed to be located 0.7 mm. into the vessel wall. This target must receive the prescribed dose. If the radiation emitted from the anode will be asymmetrically absorbed, the maximum absorption in the support structure 4 will occur where the support structure wall thickness is largest. This will in turn give an overdose to the tissue that is exposed to radiation travelling through the support structure wall 4 where the thickness is smallest. Furthermore, the over dose to the vessel wall (x=0) will also change. A typical prescribed dose is 15–18 Gy. at 0.7 mm. into the vessel wall. The overdose to the vessel wall should not exceed 50 Gy.

In addition, a minimum support structure wall thickness of 200 $\mu$m has been used, because the support structure wall 4 has to be thick enough to be mechanically stable (not to break) and has to be vacuum tight. Thinner walls are possible but will be more brittle and more sensitive to gas permeation. The structure is assumed to fit into a 1.5 mm diameter circle.

Mass attenuation data are taken from the National Institute of Standards and Technology. A typical vessel diameter of 3 mm. has been used, assuming a centered radiation source. The radiation has been assumed to have a brehmsstrahlung spectrum energized at 20 kV.

EXAMPLE 1

Calculation of Absorbed Dose From a Square Geometry Element 4 in a 3 mm Vessel, in Different Directions Difference in max/min circumferentially absorbed dose:

Target tissue dose: 183% (Max dose 33 Gy if prescribed dose is 18 Gy)

Vessel surface dose: 337% (Max dose 61 Gy if prescribed dose is 18 Gy)

Figure 4:
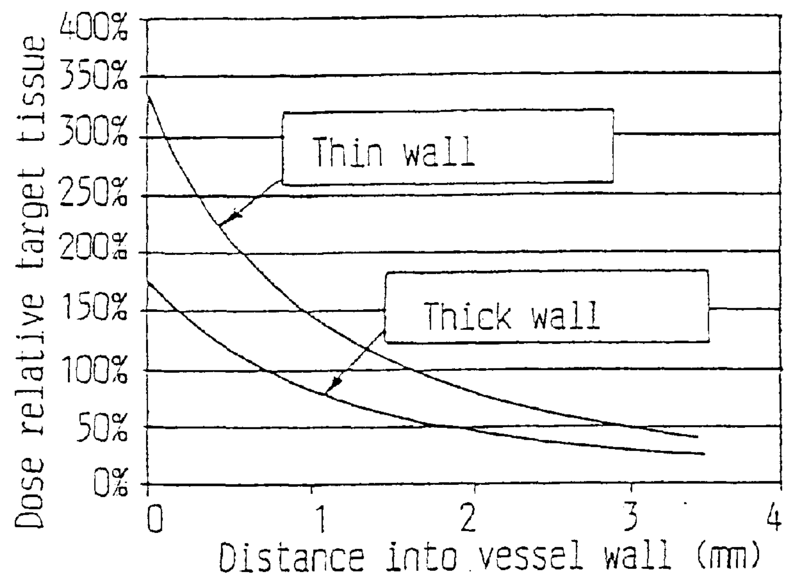
FIG. 4 shows in a graph the difference in absorbed dose in vessel wall vs. distance into the vessel wall for a square X-ray source structure where the dose is normalized to 100% at 0.7 mm for thick wall.

FIG. 4 shows the difference in absorbed dose in a graph.

EXAMPLE 2

Calculation of Absorbed Dose From a Hexagonal Geometry Element 4 in a 3 mm Vessel, in Different Directions Difference in max/min circumferentially absorbed dose:

Target tissue dose: 134%. (Max dose 24 Gy if prescribed dose is 18 Gy)

Vessel surface dose: 248% (Max dose 45 Gy if prescribed dose is 18 Gy)

Figure 5:
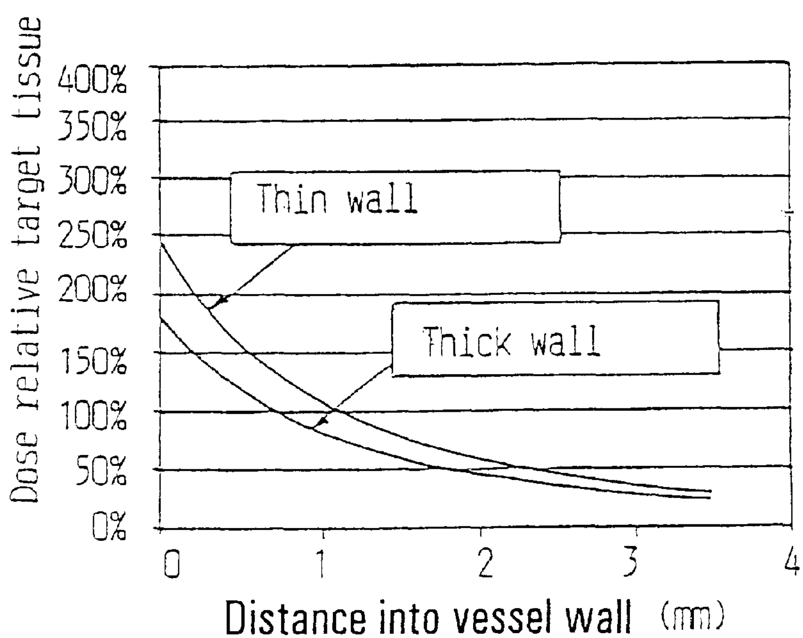
FIG. 5 shows in a graph the difference in absorbed dose in vessel wall vs. distance into the vessel wall for a hexagonal X-ray source structure where the dose is normalized to 100% at 0.7mm for thick wall.

FIG. 5 shows the difference in absorbed dose in a graph.

In addition the treatment time will be 42% longer when using a square geometry, as compared to a hexagonal geometry.

The above examples are somewhat simplified for clarity. For example a biocompatible coating (that may absorb some radiation) must be used and this has not been included in the calculations.

According to a second aspect of the present invention the presumption is that a non-uniform radiation distribution from the X-ray source is desired. For example, this may be the case if an identified treatment site is located at one side of a blood vessel.

By optimizing the form and shape of the support structure 4 a radiation window may be arranged that exhibits the highest radiation dose. This is achieved by varying the thickness of the support structure wall such that the smallest thickness is arranged where the highest radiation dose is desired, and thereby defining the position of the radiation window, and the largest thickness is arranged where the highest attenuation is wanted.

The present invention is not limited to the above-described preferred embodiments. Various alternatives, modifications and equivalents may be used. Therefore, the above embodiments should not be taken as limiting the scope of the invention, which is defined by the appending claim.

What is claimed is:

1. Miniature X-ray source comprising:

a support structure provided with a through hole; and an anode arranged at one end of the hole and a cathode at the other end of the hole, defining a cavity, wherein the anode and cathode are adapted to be energized to generate X-ray radiation, wherein the support structure has a cross-sectional shape that is adapted to transmit the generated X-ray radiation to achieve a predetermined desired radiation distribution, and wherein the support structure is a severed portion of a wafer from which a large number of support structures for X-ray sources is obtainable.

2. Miniature X-ray source according to claim 1, wherein said support structure is provided with a wall having a wall thickness between the hole and an outer side of the structure, wherein the radiation distribution depends on said wall thickness.

3. Miniature X-ray source according to claim 2, wherein the support structure has a constant wall thickness.

4. Miniature X-ray source according to claim 2, wherein the support structure has a varying wall thickness.

5. Miniature X-ray source according to claim 1, wherein a cross-sectional shape of the hole is essentially the same as the cross-sectional shape of the support structure.

6. Miniature X-ray source according to claim 1, wherein a cross-sectional shape of the hole is circular.

7. Miniature X-ray source according to claim 1, wherein a cross-sectional shape of the support structure is polygonal.

8. Miniature X-ray source according to claim 1, wherein a cross-sectional shape of the support structure is hexagonal.

9. Miniature X-ray source according to claim 1, wherein a cross-sectional shape of the support structure is octagonal.

10. Miniature X-ray source according to claim 1, wherein a cross-sectional shape of the support structure is circular.

11. Miniature X-ray source according to claim 2, wherein a part of the wall has a wall thickness with lesser thickness than the rest of the wall, defining a radiation window adapted to provide radiation at a higher dose.

12. Method of manufacturing miniature X-ray sources comprising the following steps:

i) making through holes, one for each X-ray source to be manufactured, in a disc-shaped support structure wafer having a constant thickness, ii) arranging for each hole an anode and a cathode at opposite sides of the wafer, and thereby defining an X-ray source cavity between the anode and the cathode, iii) dividing the wafer into separate elements, wherein each element includes an X-ray source adapted to generate radiation, and wherein the support structure of each X-ray source has a predefined outer shape that is determined such that a desired radiation distribution of the radiation generated by the X-ray source is achieved.

13. Method according to claim 12, wherein the holes made in step i) are made by laser drilling.

14. Method according to claim 12, wherein the holes made in step i) are made during manufacture of the wafer by moulding the wafer.

15. Method according to claim 12, wherein the holes made in step i) are made during manufacture of the wafer by precision machining.

16. Method according to claim 12, wherein in step ii) the cavity is evacuated.

17. Method according to claim 12, wherein in step iii) the wafer is divided by a sawing operation.

18. Method according to claim 12, wherein in step iii) the wafer is divided by a laser operation.

19. Method according to claim 12, wherein in step iii) the wafer is divided by a blasting operation.

20. Method according to claim 12, wherein in step iii) the wafer is divided by a scribing and cracking operation.

21. Method according to claim 12, wherein in step iii) the wafer is divided by using a preformed scribeline followed by a cracking operation.

22. A method of making a miniature X-ray source, comprising:

determining a preferred radiation distribution;

providing a radiation attenuating support structure for an X-ray source;

attaching an X-ray source to the support structure; and shaping the support structure to provide the preferred radiation distribution, wherein the support structure is a disc-shaped support structure wafer having a constant thickness, and wherein shaping the support structure comprises:

making a through-hole having a hole cross sectional shape in the wafer; and dividing the source from the wafer to provide an outer cross sectional shape for the source.

23. The method of making a miniature X-ray source as in claim 22, wherein the hole cross sectional shape is essentially the same as the outer cross sectional shape.

24. The method of making a miniature X-ray source as in claim 22, wherein the hole cross sectional shape is circular.

25. The method of making a miniature X-ray source as in claim 24, wherein the outer cross sectional shape is polygonal.

26. The method of making a miniature X-ray source as in claim 24, wherein the outer cross sectional shape is circular.

* * * * *